United States Patent
Jacobs et al.

(12) 
(10) Patent No.: US 6,682,745 B1
(45) Date of Patent: *Jan. 27, 2004

(54) USE OF BACTERIUM FOR MANUFACTURE OF A VACCINE

(76) Inventors: Christiaan Antonius Arnoldus Jacobs, Ondersteweg 2, 5995 PS Kessel (NL); Danny Goovaerts, Langenberg 18, 2460 Lichtaart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/492,206

(22) Filed: Jan. 27, 2000

Related U.S. Application Data

(63) Continuation-in-part of application No. 09/123,735, filed on Jul. 28, 1998, now Pat. No. 6,120,775.

(30) Foreign Application Priority Data

Jan. 26, 1999 (EP) .............................. 99200202

(51) Int. Cl.$^7$ ........................ A01N 63/00; A61K 49/00; A61K 39/085; A61K 39/02; C12N 7/04; C12N 1/12

(52) U.S. Cl. ................. 424/244.1; 424/93.44; 424/237.1; 424/829; 424/9.2; 435/236; 435/253.4; 435/252.1

(58) Field of Search ............... 435/252.1, 236, 435/253.4; 424/237.1, 255.1, 9.2, 244.1, 93.44, 829

(56) References Cited

U.S. PATENT DOCUMENTS

| | | | | |
|---|---|---|---|---|
| 4,521,513 A | * | 6/1985 | Russell | .................. 435/68 |
| 5,895,654 A | * | 4/1999 | Hartford et al. | ......... 424/237.1 |
| 5,895,756 A | * | 4/1999 | Barrett et al. | ............... 435/69.7 |
| 5,961,985 A | * | 10/1999 | Sprouse et al. | .......... 424/258.1 |
| 6,120,775 A | | 9/2000 | Jacobs et al. | |
| 6,344,201 B1 | * | 2/2002 | Maurelli et al. | ......... 434/234.1 |

FOREIGN PATENT DOCUMENTS

| | | |
|---|---|---|
| EP | 0 786 518 A | 7/1997 |
| EP | 0 894 500 A | 2/1999 |
| GB | 2 033 233 A | 5/1980 |

OTHER PUBLICATIONS

Curtiss III, et al., Strategies for the Use of Live Recombinant Avirulent Bacterial Vaccines for Mucosal Immunization, 1996, Academic Press, pp. 499–511.*

Titball et.al.; Vaccination against bubonic and pneumonic plague, 2001, Vaccine 19: 4175–4184.*

Haralambiev; The immunological response of calves after submucosal application of a live vaccine against parainfluenza–3– and adenovirus, 1974, 397–400.*

Curtiss R. Bacterial Infectious disease control by vaccine development. J. Clin. Invest. 110(8):1061–1066, 2002.*

Forrest. Indirect measurement of intestinal immune response to an orally administered attenuated bacterial vaccine. Infect. Immun. 60(5):2023–2029, 1992.*

Lohman B L et al: "Mucosal immunization with a live, virulence– attenuated simian immunodeficiency virus (SIV) vaccine elicits antiviral cytotoxic T lymphocytes and antibodies in rhesus macaques." Journal of Medical Primatology (Feb.–May) 23 (2–3) 95–101.

* cited by examiner

Primary Examiner—Jeffrey Fredman
Assistant Examiner—Sumesh Kaushal
(74) Attorney, Agent, or Firm—Mark W. Milstead

(57) ABSTRACT

The present invention relates to the use of live attenuated bacteria for the manufacture of a vaccine for submucosal administration.

4 Claims, No Drawings

USE OF BACTERIUM FOR MANUFACTURE OF A VACCINE

This application is a continuation-in-part of U.S. Ser. No. 09/123,735, filed Jul. 28, 1998, now U.S. Pat. No. 6,120,775, issued Sep. 19, 2000.

FIELD OF THE INVENTION

The present invention relates to the use of bacteria for the manufacture of vaccines.

BACKGROUND OF THE INVENTION

Vaccination has been proven through the years to be a very efficient method for the prevention of diseases caused by many different bacteria. Vaccines have the advantage, contrary to e.g. antibiotic or pharmacochemical therapies, that they are preventing disease rather than curing it. In many fields, e.g. the field of animal husbandry, vaccination is a standard routine. Usually, all animals in a group are vaccinated as a precautionary measure, in order to prevent disease, whereas in practice often only a few animals would have become infected if no vaccine had been given. This explains why for most commonly used vaccines adverse local reactions due to vaccination are not acceptable: it is not acceptable to cause (severe) physical stress in many animals to prevent a (mild) disease in few.

Nevertheless, for most vaccines, especially for the live vaccines that are in most cases preferable to inactivated vaccines, there is a delicate balance between a sufficiently strong triggering of the immune system on the one hand and acceptable local reactions at the site of administration of the vaccine on the other hand. As a rule of thumb, the best live vaccine gives the most severe local reactions, and therefore local reactions are often unavoidable if efficacious protection is needed.

SUMMARY OF INVENTION

It is an object of the present invention to provide ways to diminish the problem of local reactions of live vaccines without further attenuating the live vaccines.

It was surprisingly found now that when live attenuated bacteria are used for the preparation of a vaccine for administration to submucosal tissue, the thus obtained vaccine when applied submucosally gives good protection and minor local reactions.

DETAILED DESCRIPTION OF THE INVENTION

This invention is widely applicable in the field of manufacture of systemic vaccines. It is not restricted to any specific bacterium or a specific disease. Practically all live attenuated bacteria that are suitable for the manufacture of a live attenuated vaccine for systemic application are equally suitable for use in this specific invention. Systemic application comprises all applications in which the vaccine is not applied to the mucosa (mucosal application comprises i.a. oral and intranasal vaccination). Systemic application routes comprise i. a. intramuscular application (IM), subcutaneous application (SC), intradermal vaccination (ID), intravenous vaccination (IV) and intraperitoneal vaccination (IP).

Of these routes, intramuscular vaccination is in many cases the preferred application route. This is due to the fact that the vaccine, possibly mixed with an adjuvant, is only slowly released from the site of injection. Thus, the immune system is continuously triggered for a relatively long time with an immunogenic dose of the vaccine. This way of administration ensures an adequate immune response. The disadvantage, however, is, that many bacterial IM administered vaccines cause large abscesses at the site of injection. These abscesses may stay there from days to months. In those cases in which a live attenuated bacterium must behave relatively virulent in order to trigger an adequate immune response, the bacterium often replicates at the injection site to such a level that the abscess even bursts. Large intramuscular or skin/abscesses are clearly an unacceptable side-effects of vaccination with bacterial live attenuated strains, but unavoidable if further attenuation spoils the immunogenic potential of the bacterium. This causes the dilemma mentioned above, for which the invention offers a solution.

It is certainly unexpected that such soft and vulnerable tissue as submucosal tissue allows the administration of (sometimes even hardly) attenuated live bacterial vaccines.

a) without giving the unacceptable abscesses seen with intradermal or intramuscular application, while b) at the same time allowing a sufficient immune response to be build up.

This is even more unexpected if the level of damage is considered, that many relatively virulent attenuated bacteria cause to their host when given ID or IM. Intradermal or intramuscular vaccination with such bacteria often causes, next to the formation of abscesses, severe lesions at the injection site. The tissue around the injection site often completely disintegrates, leaving large scars.

All these disadvantages are hardly or not seen with the uses according to the invention.

Therefore this embodiment of the invention relates to the use of live attenuated bacteria for the manufacture of a vaccine for submucosal administration. Mucosal tissue is found i.a. in the mouth, the nose, the lining of the gut, the eye, the vulva and the lips.

Submucosal application is understood to be administration through the upper layer of the mucosa, and into the submucosa. The submucosa is a well-defined layer, known as such in the art. In principle, there is no limit to depth at which vaccination takes place (i.e. the depth of the tip of the needle), with of course the proviso that vaccination takes place in the submucosa. In practice however, the vaccine would not likely be applied deeper than about 5 millimeters from the surface of the mucosa. Generally spoken, smaller distances between the mucosa and the injection site gives smaller local effects. A very suitable depth would be in the submucosa between two and four millimeters below the mucosa.

Another attractive way of application is by using a so-called needle-less injector. The use of these injectors is known from intradermal applications, but these injectors are equally suitable for submucosal applications. Due to the softness of mucosal tissue the vaccine, when applied through a needle-less injector, goes straight through the mucosa and will come to a halt in the submucosal tissue. The depth of the vaccination only depends on the power applied during administration.

In principle, all submucosal tissue is suitable for submucosal application. In practice however, the submucosal tissue of the lips and, in female animals, the vulva are very practical sites of administration. Especially in horses, dogs and cattle the submucosal tissue of the lips would be the preferable site of administration.

Therefore, in a preferred form, the live attenuated bacteria are used for the manufacture of a vaccine for administration in the submucosa of the labiae.

As mentioned above, practically all live attenuated bacteria that are suitable for the manufacture of a live attenuated vaccine for systemic application are suitable for use in this specific invention. There are many important pathogenic bacteria for which the use according to the invention means a great improvement in safety, where the severity of local reactions is concerned. Below, a list of bacteria is presented, all known to cause abscess formation and thus severe tissue damage and skin lesions, when administered intramuscularly. And for all these bacteria there is a reciprocal relation between the decreased immunogenic potential after attenuation on the one hand, and the acceptability of local reactions at the site of administration on the other hand.

The invention applies e.g. to the use of live attenuated bacteria that are attenuated forms of horse pathogenic bacteria.

The following bacteria are examples of the large family of well-established horse pathogenic bacteria:

*Streptococcus equi*, the cause of "Strangles". This disease causes abscesses of lymph nodes of the head and neck and systemic infections. The swelling of the lymph nodes causes the horses to suffocate. No reliable vaccine without adverse local reactions is known so far for *Streptococcus equi*, *Streptococcus zooepidemicus*, causing respiratory tract infections and pneumonia, opportunistic infections and abortion in horses; *Rhodococcus equi*, causing bronchopneumonia with abscesses and intestinal abscesses; *Corynebacterium pseudotuberculosis*, causing pectoral abscesses and ulcerative lymphangitis; *Pseudomonas mallei*, causing: "Glanders", a disease characterised by pyogranulomatous inflammations, nodular lesions in lung and ulcerative and nodular lesions in skin and respiratory mucosa; *Actinobacillus equili*, a well-known cause of neonatal death, abortion in mares, stillbirth and foal septicaemia; and finally *Pasteurella multocida*, causing respiratory tract infections in horses.

Horses have in many cases both a high emotional and economical value to their owners. Especially in the field of thoroughbreds, it would be unacceptable to have horses suffering from abscesses after vaccination.

Therefore, in a more preferred form of the invention, the use relates to a use where the live attenuated bacterium is an attenuated form of a horse pathogenic bacterum.

In an even more preferred form, the live attenuated bacterium is selected from the group of bacteria comprising *Streptococcus equi, Streptococcus zooepidemicus, Rhodococcus equi, Corynebacterium pseudotuberculosis, Pseudomonas mallei, Actinobacillus equili* and *Pasteurella multocida*.

In a still even more preferred form, the live attenuated bacterium is of the species *Streptococcus equi* and/or *Streptococcus zooepidemicus*.

The invention is equally applicable to a live attenuated bacterium that is an attenuated form of a bacterium that is pathogenic for cattle.

The following list gives a number of examples of frequently encountered pathogens in cattle:

*Actinomyces pyogenes, Staphylococcus aureus, Streptococcus agalactiae* and *Streptococcus uberis, Noccardia asteroides, Corynebacterium bovis, Mycoplasma bovis,* and *Mycobacterium bovis,* all well-established causes of bovine mastitis; *Escherichia coli,* causing both bovine mastitis and diarrhoea; *Pasteurella haemolytica* and *P. multocida,* both causing pneumonia and septicaemia, *Brucella abortus,* causing abortion, *Salmonella dublin* and *S. typhimurium,* causing diarrhoea, pneumonia and systemic infections, and finally *Leptospira hardjo* as a cause of urinary tract infections.

The invention also applies to a live attenuated bacterium that is an attenuated form of a bacterium that is pathogenic for pigs.

The following list gives a few examples of pig-pathogenic bacteria:

*Streptococcus suis* causing polyserositis, *Staphylococcus aureus* causing exudative epidermitis, *Actinobacillus pleuropneumoniae* causing pleuropneumonia, *Pasteurella multocida* causing atrophic rhinitis and pneumonia, *Bordetella bronchiseptica* also causing atrophic rhinitis and pneumonia, *Escherichia coli* causing diarrhoea and edema disease, *Clostridium perfringens* as a cause of diarrhoea and septicaemia, *Salmonella cholerasuis* also a known cause of diarrhoea, *Haemophilus parasuis* also known as the cause of "Glassers disease", *Erysipelothrix rhusiopathiae* causing a disease known as "Erysipelas", *Mycoplasma hyopneumoniae* causing pneumonia, *Serpulina hyodysenteriae* as a cause of diarrhoea and *Leptospira pomona* that causes abortion.

Also, the invention applies to a live attenuated bacterium that is an attenuated form of a bacterium that is pathogenic for dogs.

Examples of such bacteria are inter alia the following bacterial dog pathogens:

*Staphylococcus aureus*, pyoderma; *Streptococcus pneumoniae*, septicaemia; *Bordetella bronchiseptica*, tracheobronchitis; *Escherichia coli*, diarrhoea; *Leptospira canicola* and *icterohaemorrhagiae*, general and urinary tract infections.

The manufactured vaccines comprise at least an immunogenically effective amount of a live attenuated bacterium. Immunogenically effective means that the amount of live attenuated bacterium administered at vaccination is sufficient to induce in the host an effective immune response of virulent forms of the bacterium.

The useful dosage to be administered will vary depending of age, weight and the type of mammal to be vaccinated, as well as the type of pathogen against which vaccination is sought. The vaccine may comprise any dose of bacteria sufficient to evoke an immune response. Doses ranging between, e.g. $10^3$ and $10^{10}$ bacteria are very suitable doses.

In addition to an immunogenically effective amount of the live attenuated bacterium described above, the manufactured vaccine also contains a pharmaceutically acceptable carrier. Such a carrier may be as simple as water, but it may e.g. also comprise culture fluid in which the bacteria were cultured. Another suitable carrier is e.g. a solution of physiological salt concentration. Other examples of pharmaceutically acceptable carriers or diluents useful in the present invention include stabilisers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity may be added to the vaccine. Adjuvants are non-specific stimulators of the immune system. They enhance the immune response of the host to the invading pathogen. Examples of adjuvants known in the art are Freunds Complete and Incomplete adjuvants, vitamin E, non-ionic block polymers, muramyldipeptides, ISCOMs (immune stimulating complexes, cf. for instance European Patent EP 109942), Saponins, mineral oil, vegetable oil, and Carbopol (a homopolymer). Other suitable adjuvants are for example aluminium hydroxide, phosphate or oxide, oil-emulsions (e.g. of Bayol F$^{(R)}$ or Marcol 52 $^{(R)}$, saponins or vitamin-E solubilisate.

EXAMPLES

Example 1

Comparison of Safety of Intramuscular and Submucosal Administration of Two Different Attenuated *Streptococcus equi* Strains In this experiment the safety and efficacy of live *S. equi* strain TW 928 deletion mutant vaccine and of strain TW 928/sls double mutant vaccine in Diluvac Forte® (obtainable through Intervet Int. B.V., P.O. Box 31, 5830 AA Boxmeer, The Netherlands), both administered submucosally in the lip, were tested. A comparison with the safety of a similar intramuscular vaccination has been made.

After a 2 weeks acclimatisation period, 5 horses were vaccinated submucosally in the lip with strain TW 928 deletion mutant. Vaccination was done at 2 spots in the upper lip and 2 spots in the lower lip. A needle was used that was provided with a disc of about 1 centimeter diameter, attached at right angles to the needle, and located at about 2.5 millimeters from the tip of the needle. This prevented the tip of the needle from entering the submucosa anymore than about 2 millimeters.

A volume of 200 µl of the vaccine, comprising $10^{8.8}$ bacteria was given at each spot.

Three other horses were vaccinated subcutaneously in the same way, but with a double mutant: strain TW 928/sls comprising $10^{8.2}$ bacteria in Diluvac Forte.

Three horses were vaccinated IM in the neck with comparable doses of the TW 928 deletion mutant strain.

Two horses were left as controls.

At 4 weeks after priming vaccination the vaccinates, were boosted as described above with the same amount of bacteria at similar vaccination sites. At 2 weeks after booster vaccination, all horses were challenged intranasally with $7.7\times10^8$ CFU of the challenge strain *S. equi* strain Arnica in a 2 ml volume. After vaccination the horses were observed for any systemic or local reactions and after challenge, the horses were examined for clinical signs of strangles or any other abnormality.

Results

Horses subjected to intramuscular vaccination in the neck developed large abscesses that reached diameters ranging between 10 and 30 centimeters within weeks after vaccination. These abscesses were persistent and kept growing until they burst.

Horses subjected to submucosal vaccination appeared in a good condition and had a normal appetite, and no significant further systemic reactions were observed.

After submucosal priming and boosting with the 928 deletion mutant, only small and transient local reactions were found. Most reactions had disappeared at 3 weeks after priming vaccination and at 2 weeks after booster vaccination. The same minor local reactions, but to an even lesser extend, were observed after both vaccinations with the 928/sls double mutant.

After challenge, the five horses vaccinated submucosally with the TW 928 deletion mutant appeared completely protected. Complete protection was also obtained in the horses vaccinated intramuscularly with the TW 928 deletion mutant.

Therefore it can be concluded that full protection can be obtained with suitable vaccine strains regardless the site of administration, intramuscularly or submucosally.

hardly any adverse local reactions are found at the site of submucosal administration, whereas intramuscular administration causes large persistent abscesses at the site of administration.

Example 2

Comparison of Submucosal and Intramuscular Administration of a Strain of the Horse Pathogenic Bacterium *Streptococcus zooepidemicus*

In this experiment the safety of submucosal administration of *Strep. z.* was compared to that of intramuscular administration, especially with respect to adverse local reactions.

Two horses were vaccinated submucosally in the lip with $7\times10^7$ CFU *Strep. z.* in a total volume of 0.2 ml. Two other horses were vaccinated intramuscularly in the neck with the same dose, but in a total volume of 1 ml.

Results

The intramuscularly vaccinated horses developed large abscesses from the fourth day after vaccination, that grew to an average size, at ten days after vaccination, of about 20 centimeters diameter. These abscesses were persistent.

The submucosally vaccinated horses only developed minor abscesses with an average size of 2.5 centimeters beginning at day 5 after vaccination. The abscesses completely disappeared after six days, leaving no traces behind.

Example 3

Comparison of Submucosal and Intramuscular Administration of a Virulent Strain of the Bovine Pathogenic Bacterium *Actinomyces pyogenes*

In this experiment the safety of submucosal administration of *A. pyogenes* was compared to that of intramuscular administration, especially with respect to adverse local reactions.

Two cows were vaccinated submucosally in the vulva with $1.2\times10^{10}$ CFU in a total volume of 0.2 ml, Two other cows were vaccinated intramuscularly in the neck with the same dose, but in a total volume of 1 ml.

Results

In the submucosally vaccinated animals, small abscesses developed after three days, reaching an average diameter of about 3.5 centimeters . These abscesses decreased in size after a few days.

In the two cows vaccinated intramuscularly in the neck with the same dose, large and more persistent abscesses developed after three days, reaching a diameter of between 9 and 14 centimeters.

What is claimed is:

1. A method for administering a live attenuated bacterial vaccine to a mammal, comprising:

injecting into a submucosal tissue of a mammal an immunogenically effective amount of a live attenuated bacterium, wherein said live attenuated bacterium is selected from the group consisting of *Streptococcus equi* and *Streptococcus zooepidemicus.*

2. The method according to claim 1, wherein said vaccine is administered into the submucosa of the labiae.

3. A method for reducing the amount of adverse reactions in a mammal at an injection site of a live attenuated bacterial vaccine, comprising:

administering by injection into submucosal tissue of said mammal said vaccine, wherein the amount of adverse reactions at the injection site is reduced, wherein the reduction is measured by the amount or size of abscesses or lesions at the mucosal injection site compared to an intramuscular injection site, wherein said live attenuated bacterium is selected from the group consisting of *Streptococcus equi* and *Streptococcus zooepidemicus.*

4. The method according to claim 3, wherein said vaccine is administered into the submucosa of the labiae.

* * * * *